US005736106A

United States Patent [19]

Ishiguro et al.

[11] Patent Number: 5,736,106

[45] Date of Patent: Apr. 7, 1998

[54] THERMAL CYCLING REACTION APPARATUS AND REACTOR THEREFOR

[75] Inventors: Takahiko Ishiguro, Kanagawa; Shingo Fukunaga, Tokyo; Yasutami Mitoma, Kanagawa, all of Japan

[73] Assignee: Tosoh Corporation, Shinnanyo, Japan

[21] Appl. No.: 591,270

[22] Filed: Jan. 25, 1996

[30] Foreign Application Priority Data

Jan. 26, 1995 [JP] Japan .................................... 7-010636

[51] Int. Cl.$^{6}$ .............................. B01L 3/00; C12P 19/34; C12M 3/04; C12M 1/40

[52] U.S. Cl. .......................... 422/131; 422/99; 422/68.1; 435/91.2; 435/91.1; 435/285.1; 435/287.2; 435/288.7; 165/133; 165/64

[58] Field of Search ................................ 435/91.1, 91.2, 435/285.1, 287.2, 288.7; 165/133, 64; 422/99, 68.1, 131

[56] References Cited

U.S. PATENT DOCUMENTS

| | | | |
|---|---|---|---|
| 4,284,725 | 8/1981 | Fennel et al. | 435/301 |
| 4,602,681 | 7/1986 | Daikoku et al. | 165/33 |
| 5,435,378 | 7/1995 | Heine et al. | 165/64 |
| 5,455,175 | 10/1995 | Wittwer et al. | 435/286.1 |
| 5,460,780 | 10/1995 | Devaney et al. | 422/99 |
| 5,498,392 | 3/1996 | Wilding et al. | 422/68.1 |
| 5,504,007 | 4/1996 | Haynes | 435/285.1 |
| 5,508,197 | 4/1996 | Hansen et al. | 435/235.1 |
| 5,525,300 | 6/1996 | Dannssaert et al. | 422/99 |

FOREIGN PATENT DOCUMENTS

| | | |
|---|---|---|
| 0 318 255 | 5/1989 | European Pat. Off. . |
| 0 524 808 | 1/1993 | European Pat. Off. . |
| 88 13 773 | 2/1989 | Germany . |

OTHER PUBLICATIONS

Clinical Chemistry, vol. 40, No. 9, pp. 1815–1818, 1994, Peter Wilding, et al., "PCR in a Silicon Microstructure".

*Primary Examiner*—W. Gary Jones
*Assistant Examiner*—Dianne Rees
*Attorney, Agent, or Firm*—Oblon, Spivak, McClelland, Maier & Neustadt, P.C.

[57] ABSTRACT

A thermal cycling reaction apparatus comprises a reactor having a reactor body made of a thin heat-conductive plate having a cavity as a reaction chamber with an opening of the chamber sealed with a transparent heat-resistant sheet. The apparatus further includes, delivery rollers for delivering the reactor along a delivery path and stopping it at stopping positions in a predetermined order; plural temperature-controlling blocks having respectively a temperature-controlling surface to be brought into contact with a heat-transfer face of the reactor and being placed at the stopping positions separately so as not to thermally affect each other; and a temperature-controlling mechanism for keeping the fixed temperature-controlling surfaces respectively at prescribed temperatures.

11 Claims, 3 Drawing Sheets

FIG. 1A
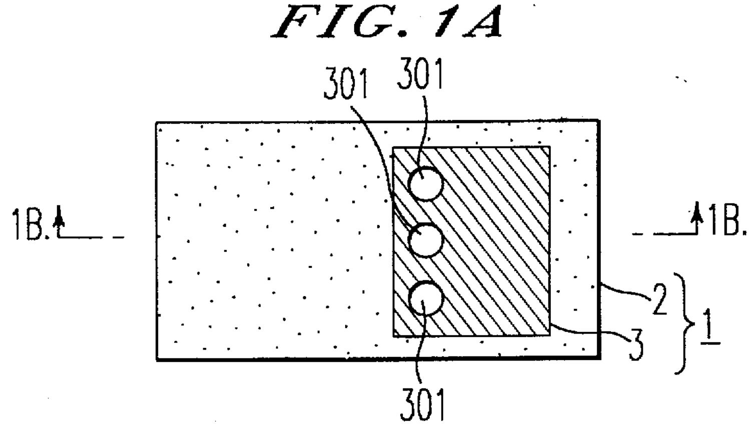
FIG. 1B
FIG. 1C
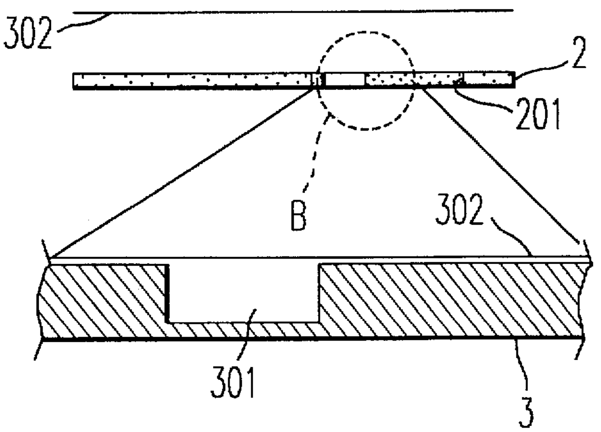
FIG. 2
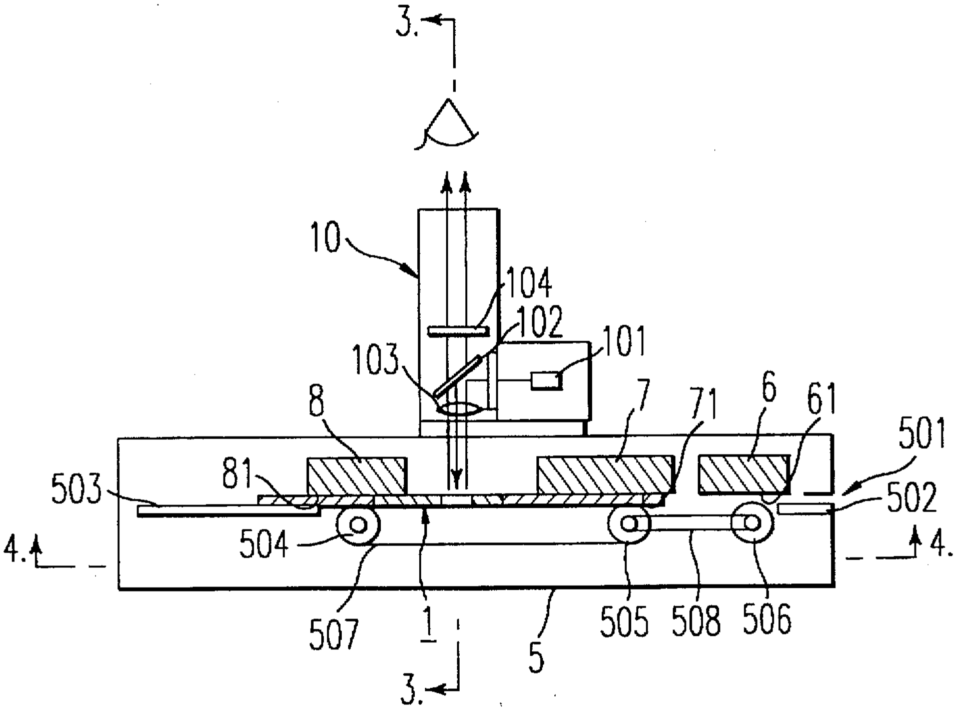

THERMAL CYCLING REACTION APPARATUS AND REACTOR THEREFOR

BACKGROUND OF THE INVENTION

1. Field of the Invention

The present invention relates to a thermal cycling reaction apparatus which is useful for polymerase chain reactions (PCR) and other thermal cycling reactions, and to a reactor (reaction vessel) suitable therefor.

2. Description of the Related Art

The PCR technique for amplification of a target DNA sequence is known in which a specific target gene is amplified in a large amount in a short time by annealing two kinds of primers respectively to the ends of the target DNA fragment, and repeating a template-specific DNA synthesis reaction with a DNA polymerase in vitro (Japanese Patent Publications 4-67957, 4-67960, etc.). This technique makes it practicable to detect a DNA or a DNA-containing microorganism existing only few in number. Therefore, the PCR technique is widely employed in various technical fields such as biochemistry, biology in a broad sense including genetic engineering, medical science, pharmacology, and agriculture.

The PCR method, generally, is employed for amplifying a DNA from a few number of molecules to a larger number of molecules by repeating many times a cycle of three-step thermal profile (raising and lowering of the temperature) including a first step of keeping a DNA having a targeted DNA sequence at a dissociation temperature (or denaturation temperature) to dissociate the double-stranded DNA into a single-stranded DNA; a second step of keeping the single-stranded DNA at an annealing temperature to anneal thereto a forward primer and a reverse primer; and a third step of keeping the reaction liquid at a temperature for complementary DNA synthesis to sequentially now the DNA complementary to the single-stranded DNA.

The PCR is conventionally conducted by use of a computer-controlled automatic temperature-cycling apparatus (a thermal cycler). In an example, an apparatus equipped with such a thermal cycler comprises a metal block which has a bath (cavity) for a holding reaction chamber containing therein a reaction mixture, and a high-temperature fluid storage vessel and a low-temperature fluid storage vessel connected to flow paths to circulate a heating fluid through the metal block. Thereby the temperature of the reaction mixture is automatically changed successively through the aforementioned three steps of prescribed temperatures by switching over the flows of the high-temperature fluid and the low-temperature fluid introduced into the bath in the above metal block: for example, at 90°–95° C. for about 20 seconds in the first step (denaturation), at 45°–60° C. for about 20 seconds in the second step (annealing), and 65°–75° C. for about 30 seconds in the third step (DNA synthesis).

In another example of the thermal cycler, not for PCR, 100 test-tube type reaction chambers, for instance, which are hung from a rack are transferred successively to five thermostats holding a heating medium of different temperatures, and are dipped therein to conduct a desired enzymatic reaction, enzyme deactivation, or other enzymatic cycling reactions in the respective thermostats (Japanese Patent Publication 62-12986).

The aforementioned thermal cycler, which changes the temperature of the reaction mixture for the respective steps by raising or lowering the temperature of the heating bath medium in the metal block by switching the circulation of temperature-controlling fluids, has disadvantages as follows. The simple switchover of a heating medium of the temperature for the one step to another heating medium of the temperature of the succeeding step, for example from 90° C. for the first step to 45° C. for the second step, results in a significantly low rate of temperature change in comparison with the time for the intended reaction, and repetition of the cycles many times requires an extremely long time for the entire treatment. Further, the reaction of the first step (also of the second step) proceeds not only at the set temperature (90° C.) but also in a temperature range of several degrees centigrade around the set temperature, which renders it difficult to control the reaction in the prescribed time. In an extreme case, the reaction does not proceed at all, disadvantageously.

In order to change the temperature quickly for the subsequent step, for example in the above case, a fluid at a temperature sufficiently lower than the prescribed temperature of the second step can be circulated to the bath, and later circulate a fluid corresponding to the prescribed temperature. In such a method, the temperature of the reaction mixture is liable to become lower than the prescribed temperature to cause a so-called overshooting at the end stage of cooling from 90° C. to 45° C. This will impair the reproducibility of the reaction, and in an extreme case, the process does not proceed, disadvantageously. Moreover, this method requires additionally a thermostat, a fluid storage vessel, and piping for the high-temperature or low-temperature fluid, which renders it difficult to miniaturize the apparatus, and is not suitable for simultaneous treatment of many samples.

On the other hand, the latter of the aforementioned systems, in which test tubes hung from a rack are successively delivered and immersed into plural thermostats holding fluids of different set temperatures, requires a mechanical means for delivering and immersing the test tubes, whereby the apparatus becomes larger, and the rapid temperature changes are not readily achievable between the prescribed temperatures.

SUMMARY OF THE INVENTION

The present invention has been achieved to overcome the above disadvantages of conventional thermal cyclers employed in thermal cycling reactions by employing a novel thermal cycling reaction apparatus and a reaction chamber suitable therefor.

A first object of the present invention is to provide a thermal cycling reaction apparatus which allows rapid temperature changes through prescribed temperature steps to shorten the time of a repeated thermal cycling reaction, and to provide a reaction chamber therefor.

A second object of the present invention is to provide a thermal cycling reaction apparatus which is capable of keeping the entire reactor at a uniform temperature and avoiding the disadvantage of nonuniformity, in simultaneous treatment of plural samples under the same conditions, in the amount of the reaction product and the reaction progress, independently of the location of the reaction chambers in the reactor, and to provide a reactor suitable therefor.

A third object of the present invention is to provide a thermal cycling reaction apparatus which is capable of raising or lowering the reaction liquid temperature to a prescribed temperature without overshooting, and enables easy control or omission of a temperature controller, and to provide a reactor suitable therefor. Thereby, the precision of control of the temperature and time of reaction is improved.

A fourth object of the present invention is to provide a thermal cycling reaction apparatus which can be miniaturized by miniaturizing the temperature controller for the reaction liquid by employing a smaller amount of a reaction liquid sealed in a smaller chamber, and to provide a reactor suitable therefor.

A fifth object of the present invention is to provide a thermal cycling reaction apparatus for a PCR process which repeats many times a temperature change cycle comprising successive steps of keeping a reaction liquid at a first temperature for dissociating or denaturing a double-stranded DNA having a target DNA sequence into a single-stranded DNA; keeping it at a second temperature for bonding or annealing a normal-directional primer and a reverse-directional primer to the resulting single-stranded DNA; and keeping it at a third temperature for synthesizing another DNA sequence complementary to the single-stranded DNA in the presence of a DNA polymerase, and to provide a reactor therefor. Thereby, the pre-heating or pre-cooling of the PCR reaction liquid in each step can be substantially omitted to shorten the overall reaction time, and the reaction can be allowed to proceed in a completely sealed chamber to avoid the PCR products and to avoid the contamination caused from aerosol amplified DNA.

BRIEF DESCRIPTION OF THE DRAWINGS

FIGS. 1A to 1C show schematically a reactor of the present invention used for a thermal cycling reaction. FIG. 1A is a plan view of the reactor, FIG. 1B is a sectional view of the reactor taken along line A—A in FIG. 1A, and FIG. 1C is an enlarged view of the portion B in FIG. 1B.

FIG. 2 is a schematic sectional front view of an example of the thermal cycling reaction apparatus of the present invention employing the reactor shown in FIGS. 1A to 1C.

FIG. 5A shows the stopping positions during the cycling reaction, and FIG. 5B shows the stopping positions for the optical measurement.

DETAILED DESCRIPTION OF THE PREFERRED EMBODIMENT

Figure 3:
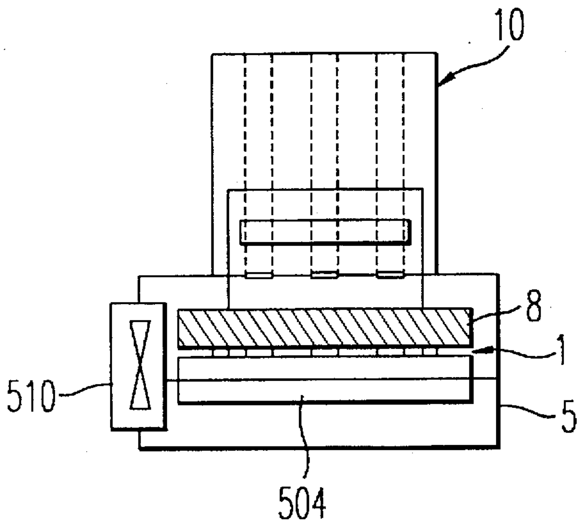
FIG. 3 is a right-hand side view of the apparatus shown in FIG. 2 taken along line C—C.

The reactor of the present invention employed for a thermal cycling reaction is delivered, along a delivery path having plural and separate temperature-controlling blocks fixed thereon and having respectively a fixed temperature-controlling surface of a prescribed area at a controlled temperature, to contact successively with the temperature-controlling blocks in a predetermined order repeatedly: the reactor comprising a reactor body in a shape of a thin plate, having a heat-transfer area on at least one face of the thin plate to be brought into face-to-face contact with the respective temperature-controlling surfaces, and having a cavity of a small volume as a reaction chamber in the thickness of the thin plate having an opening on one face or both faces of the thin plate; and a heat-resistant sealing sheet for sealing the reaction chamber by covering the opening of the chamber.

In the above consititution, when an optical detection system is employed to detect the change in the reaction liquid, the sealing sheet for the reaction chamber is preferably a transparent heat-resistant sheet to form a light-transmitting window.

The aforementioned reactor may be in a shape of a thin plate of a heat-conductive material such as aluminum and other metals, or may be constituted by a combination of the above reactor body made of the heat-conductive material with a delivery-assisting member made of a poor heat-conductive material such as nylon, polycarbonate, and other plastic materials. The delivery-assisting member of a poor heat-conductive material may be combined to form a thin plate with the reactor body in its entirety, but is not limited thereto. The shape of the delivery-assisting member may be selected to have a shape or structure suitable for the type of the delivery means. For example, the reactor body may be combined with a surface of the delivery-assisting member in a rotor or drum shape to be delivered by rotation of the rotor or the drum. In a preferred example in which the reactor body is combined with the delivery-assisting member, the thin plate-shaped reactor body made of a heat-conductive material is fitted and fixed into a recess or an opening formed on the delivery-assisting member in a plate, rotor, or drum shape. Naturally, a member may be employed or an operation may be conducted for fixing the reactor.

The heat-conductive material suitable for constructing the reactor in the present invention includes the materials which have a sufficient thermal conductivity for bringing the reaction chamber quickly to an intended temperature level, preferably having a thermal conductivity of not lower than 20 kcal/m·h·° C. such as metallic materials like the aforementioned aluminum. On the other hand, the poor heat-conductive material (heat-insulating material) for constructing the delivery-assisting member, provided as desired, includes the materials which have a sufficiently low thermal conductivity for maintaining the temperature of the reactor body, preferably having a thermal conductivity of not higher than 0.5 kcal/m·h·° C. such as plastic materials like the aforementioned polycarbonate.

The reactor body may be formed into any suitable shape as desired, such as a rectangular plate, a circular plate, a flat plate, and a curved plate to be fitted to a drum surface. The size of the reactor is not limited. Generally, the thickness ranges preferably from 0.2 to 3 mm, more preferably from 0.2 to 2 mm for rapid temperature change of the reaction liquid and uniform temperature distribution therein. When the reactor is in a rectangular plate shape, the width ranges preferably from 20 to 40 mm, and the length ranges preferably from 50 to 100 mm.

The reaction chamber in the reactor body is formed as a cavity in the thickness of the plate. Generally the chamber is a bottomed hole having an opening on the one face of the thin plate, or a through hole piercing the plate for ease of working of the reactor. The opening or openings are sealed liquid-tight against the outside air with a sealing sheet. The opening is generally in a shape of a circle of a diameter ranging from 10 to 20 mm, preferably from 14 to 18 mm, but is not limited thereto. The reaction chamber may be provided singly or in plurality separately in one reactor. The volume of the chamber is about 0.1 mL, preferably in the range of from 0.01 to 0.2 mL for rapid temperature change.

The sealing sheet for sealing the opening of the reaction chamber may be made of any material which has sufficient resistance to heat, chemicals, and so forth, and does not cause deformation of the sheet or elution of an impurity therefrom. In particular, for optical measurement of the results of the reaction, preferably employed is a sheet transparent or at least transparent at the measurement wave length of a material such as an acrylic resin, polyethylene, and a vinyl chloride resin. The sheet may be a flexible film or a rigid plate.

The reactor body preferably has a hole for filling the reaction liquid. In particular, the filling hole has a structure to ensure sealing after filling of the reaction liquid. Examples of a suitable structure of the filling hole include a filling pathway at the side face of the reactor body and heat-sealable after filling of the liquid; a sealable one-way valve which allows only liquid filling and a rubber plug for filling the liquid by an injection needle and capable of restoring a liquid-tight state after removing the needle.

The reaction chamber is formed in a heat-transferring area of the reactor body in order to bring the reaction chamber into direct contact with a fixed temperature-controlling surface. The portion to be contacted with the fixed temperature-controlling surface may be at the chamber opening side or at the side having no chamber opening of the reactor body. The heat-transferring area may be provided on one face of the reactor body or may be provided on both faces of the reactor body in order to be contacted with the fixed temperature-controlling surfaces provided in a pair on both sides of a delivery path. The heat-transferring area is designed to be sufficient to rapidly transfer the heat between the fixed temperature-controlling surface and the entire reactor body. The size of the heat-transferring area to be contacted with the fixed temperature-controlling source is not specially limited. Usually the entire of the one face of the reactor body, or a limited area around the reaction chamber is brought into face-to-face contact with the fixed temperature-controlling surface.

The feature of the thermal cycling reaction apparatus of the present invention is described below. The thermal cycling reaction apparatus comprises a reactor body constituted of a thin plate of heat-conductive material having a cavity with at least one opening sealed by a sealing sheet on a surface of the reactor, or the reactor body supported by delivery-assisting member; a delivery path for guiding the reactor; plural temperature-controlling blocks placed apart from each other so as not to cause thermal interaction along the delivery path and having respectively a fixed temperature-controlling surface of a prescribed area to be brought into contact with the reactor; a temperature-controlling means for maintaining the temperature-controlling surfaces of the temperature-controlling blocks at respectively prescribed temperatures; and a driving means for delivering and stopping the reactor to come into contact with each of the fixed temperature-controlling surfaces of the temperature-controlling blocks in a predetermined order repeatedly.

As an additional feature, the thermal cycling reaction apparatus of the present invention may further comprise an optical detecting means for detecting optically the change in the reaction chamber, such as a degree of progress of the reaction, through the aforementioned transparent sealing sheet by stopping the reactor at a position other than the temperature-controlling block positions. With this constitution, the optical detecting means enables monitoring of the progress of the reaction with lapse of time, or measuring optically the state of the reaction mixture after the end of the reaction.

The optical detecting means for detecting optically the change in the reaction liquid includes known conventional optical means such as the one which introduces light reflected by a half mirror into the reaction chamber and observes the light reflected from the chamber through the half mirror visually, or by a light-receiving means like an optical sensor, or an image pick-up means such as a video camera, but is not limited thereto.

The delivery path for guiding the movement of the reactor in the apparatus of the above constitution is typically a linear path for carrying the reactor linearly in a reciprocating manner by employing a device such as a guide rail, and a guide roller. Otherwise, the delivery path may be a circular or arc-shaped path for rotating the reactor around an axis by using a rotor type or a drum type of delivery-assisting member.

The fixed temperature-controlling surface of the above apparatus is formed as a surface of the temperature-controlling block so as to come into contact with the heat-transferring area provided on the one or both faces of the reactor. The temperature-controlling surface is not limited in its shape, and may be planar, curved, rugged, or in any other shape, provided that the surface is capable of coming into close contact with the heat-transferring area. The material for the temperature-controlling block includes metals, plastics, rubbers, ceramics, and the like, and is not specially limited. However, the material and the structure are preferred which has sufficient heat capacity not to cause large temperature change by heat exchange on contact with the reactor. The fixed temperature-controlling surfaces are separated so as not to interact thermally with each other. For this purpose, the distance between the surfaces may be kept larger, or a heat-insulating plate may be provided between the temperature-controlling blocks. For ensuring close contact between the fixed temperature-controlling surface of the temperature-controlling block and the reactor, and for ensuring smooth delivery of the reactor, a certain gap is preferably provided between the reactor, and the fixed temperature-controlling surface during delivering of the reactor, and the reactor is pushed against the fixed temperature-controlling surface at the time of stopping by a pressing means such as a cylinder mechanism. The temperature-controlling blocks are placed on one side of the delivery path in the case where the reactor is brought into contact with them on one face, or are placed in pairs on both sides of the delivery path in the case where the reactor is brought into contact with them on both faces.

The temperature-controlling means may be of any type of electric heating, circulation of a heating liquid medium, and the like. Of these, the electric heating is preferred in simplicity and for miniaturization of the apparatus. The temperature control may be conducted to maintain an intended constant temperature by use of a sensor like a thermal sensor by on-off control of the heating source.

The driving means for delivering the reactor may be constructed, for example, from a combination of devices comprising a delivering device such as a roller for delivery of the reactor along the delivery path provided by the guiding device; a driving device for driving the delivering device such as a roller for driving and stopping it to deliver and stop the reactor at the prescribed positions; and a drive-controlling device for controlling the drive according to a sequence program or the like following prescribed steps. The thermal cycling reaction can be automated and mechanized by employing an MPU (microprocessor unit) for the drive-controlling means.

The thermal cycling reaction apparatus of the present invention, as described above, is useful for PCR or the like reactions. Specifically, the first, second, and third fixed temperature-controlling surfaces are provided. The first temperature-controlling surface is kept at a dissociation temperature (or denaturation temperature) of a DNA having a target DNA sequence to dissociate the double-stranded DNA into a single-stranded DNA. The second temperature-controlling surface is kept at an annealing temperature for the single-stranded DNA to anneal thereto a normal-directional primer and a reverse-directional primer. The third temperature-controlling surface is kept at a temperature for complementary DNA synthesis to grow sequentially the DNA complementary to the single-stranded DNA. The delivering means is constructed to deliver the reactor intermittently to the first, second, and third fixed temperature-controlling surfaces. This cycle of the steps is repeated a number of times. Thus the PCR can be readily and surely conducted.

The PCR conducted according to the present invention is not limited to the above-mentioned type of reaction. Various modifications of PCR can be conducted with the thermal cycling reaction apparatus and reactor of the present invention. For example, a two-temperature PCR, namely a simplified PCR in which the annealing of the primers and synthesis by DNA polymerase are conducted at the same temperature, and denaturation is conducted at a higher temperature, can be conducted by arranging temperature-controlling blocks corresponding to the respective temperatures with the apparatus and the reactor of the present invention.

Thermal cycling reactions other than the PCR, for example the enzymatic cycling reaction mentioned before (Japanese Patent Publication 62-12986), can be conducted with the reactor and the thermal cycling reaction apparatus of the present invention.

According to the present invention, the reaction liquid sealed in the reaction chamber formed in the thickness of a thin plate is brought into contact successively with the surfaces of plural temperature-controlling blocks kept at prescribed temperatures, and by this contact, the temperature of the reaction liquid is controlled precisely by the fixed surfaces of the temperature-controlling blocks.

The typical thermal cycling reaction apparatus for PCR is explained below by reference to the drawings.

FIGS. 1A to 1C show schematically the reactor of the present invention used for a thermal cycling reaction. FIG. 1A is a plan view, FIG. 1B is a sectional view of the reactor taken along line A—A in FIG. 1A, and FIG. 1C is an enlarged sectional view of the portion B in FIG. 1B.

In the drawings, the reactor 1 comprises a delivery-assisting member 2 made of a heat-insulating acrylic resin in a shape of a rectangular plate, and a reactor body 3 made of heat-conductive aluminum in a shape of a rectangular plate and is fitted to a through hole 201 of the delivery-assisting member 2. The planar rectangular through hole 201 is formed at a position deviating in a length direction (lateral in FIG. 1) from the center of the member (rightward in FIG. 1), where the reactor body 3 is fitted. The reactor body 3, in this example, has three independent reaction chambers 301 in a shape of bottomed round recess (empty space). The one face of the reactor body 3 is covered entirely with a sealing sheet 302 made of a transparent heat-resistant polyethylene to seal the reaction chambers 301. In this example, the delivery-assisting member 2 of the reactor 1 is 130 mm in length, 85 mm in width, and 1.5 mm in thickness; the reactor body 3 is 25 mm in length, 70 mm in width, and 1.5 mm in thickness; and the reaction chamber 301 is 8 mm in radius, and 1 mm in depth, and a small volume of 0.2 mL.

In this example, the reaction liquid is filled into the reaction chambers 301 of the thin plate reactor 1, and then the sealing sheet 302 is placed thereon, and heat-sealed to enclose the reaction liquid.

Figure 4:
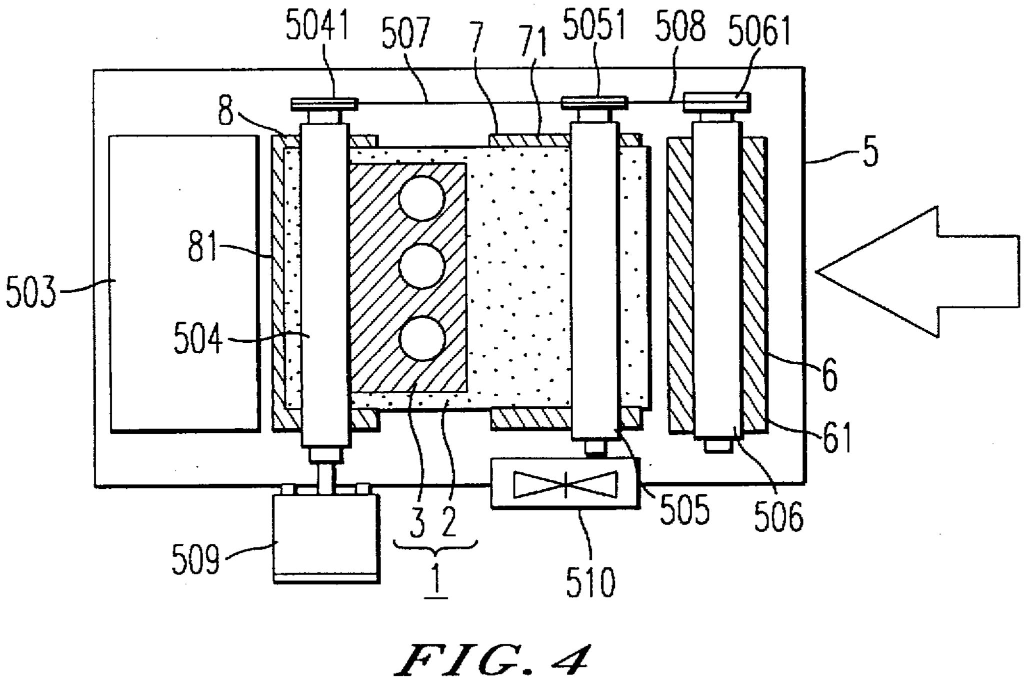
FIG. 4 is a bottom end view of the apparatus shown in FIG. 2 taken along line D—D.

FIGS. 2 to 4 illustrates schematically an example of a thermal cycling reaction apparatus. On a lateral face of a casing 5 in a flat box shaper a slit-shaped gateway 501 and a gateway guide 502 are provided at a predetermined height for introducing and removing a reactor. Near the inside wall opposite to the gateway guide 502, a leading guide 503 is provided at the same height as the gateway guide 502. Between the gateway guide 502 and the leading guide 503, a driving roller 504, a driven rollers 505, 506, are placed at prescribed intervals. The rollers 504, 505, 506 are allowed to rotate by pulleys 5041, 5051, 5061 (FIG. 4) provided at respective ends of the axes of the rollers, and belts 507, 508 put on the pulleys synchronously driven by a motor 509. The internal space is ventilated with a fan 510.

Four stopping positions are set along the delivery direction of the horizontal linear delivery path defined by the three rollers 504, 505, 506, the gateway guide 502, and the leading guide 503. In this example, successively from the right in FIG. 2, are placed a first temperature-controlling block 6, a second temperature-controlling block 7, and a fourth temperature-controlling block 8 respectively at the first, second and third stopping positions at the upper side of the delivery path, and an optical detector 10 is placed above the third stopping position to measure the change in the reaction chamber. The temperature-controlling blocks 6 to 8 are constituted respectively of an aluminum block and an electric heater embedded therein.

On the lower faces of the temperature-controlling blocks 6, 7, 8, fixed temperature-controlling surfaces 61, 71, 81 are formed respectively for contact with the upper face of the reactor 1 so as to keep the reaction liquid in the reaction chamber 301 of the reactor stopped in a contacting state at a prescribed temperature. In order to achieve close contact between the temperature-controlling surface and the reactor, a slight play in vertical direction may be given to the temperature-controlling block, or downward spring force may be applied to the temperature-controlling block to collide against the reactor, or a vertically directed pressing mechanism may be provided on either one of them. In this example, the temperature-controlling blocks are placed at intervals of 10 mm or more to avoid thermal interaction between the blocks.

The temperature of the fixed temperature-controlling surface can be controlled at a prescribed level by a conventional method. In this example, an electric heater is incorporated into the temperature-controlling block, and the heater is turned on and off following the temperature detected by a sensor.

The optical detector 10 provided at the third stopping position comprises a light source 101, a half mirror 102, a lens 103, and a spectrometric filter 104. With this optical detector, the degree of the progress of the reaction in the reaction liquid in the chamber is monitored visually with lapse of time.

Figure 5A:
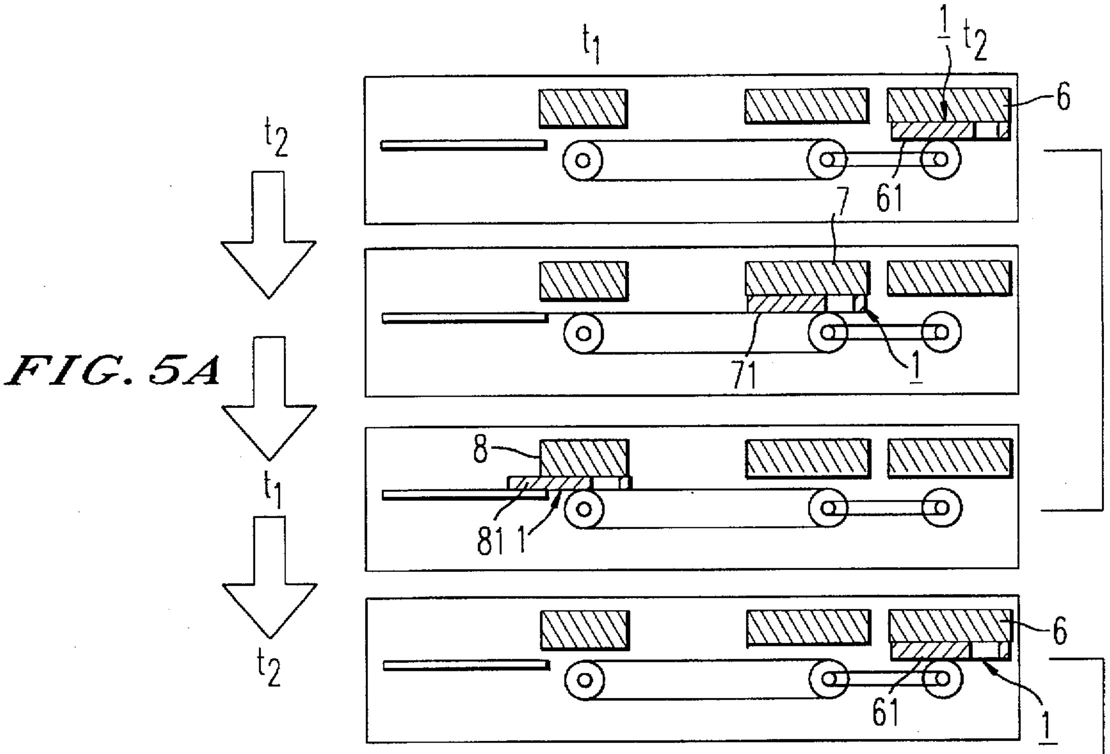
FIGS. 5A and 5B are schematic diagrams showing the successive stopping positions of the reactor in a thermal cycling reaction and optical measurement with the reaction apparatus of FIG. 2.
Figure 5B:
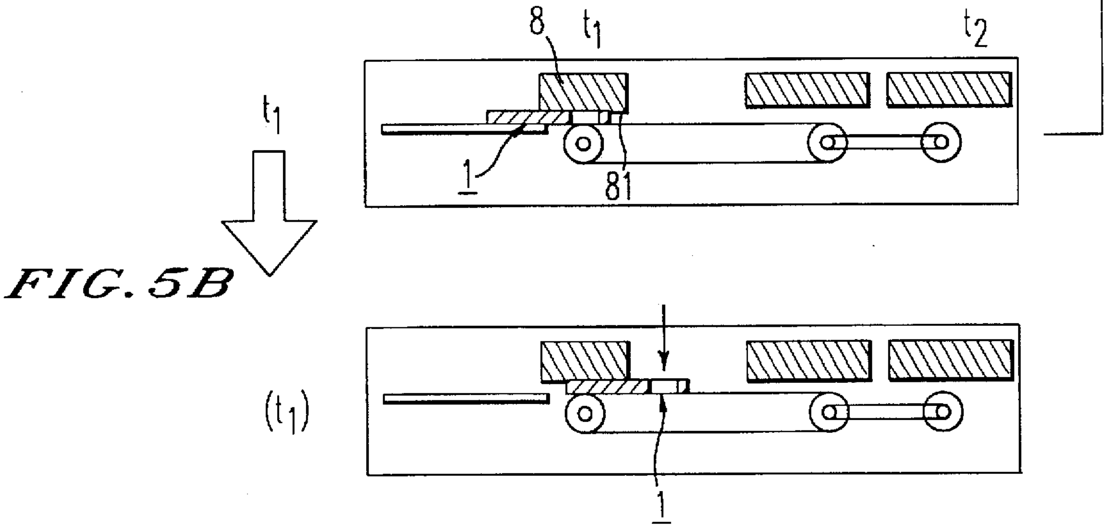

FIGS. 5A and 5B are schematic diagrams for explaining an example of operation of the thermal cycling reaction with the above-described apparatus. In FIG. 5A–5B, for simplicity, only the reactor body 3 of the reactor assembly is shown.

In this example, the reactor 1 is brought into face-to-face contact with the first temperature-controlling block 6 having a fixed temperature-controlling surface 61 kept at a temperature $t_2$ (90° C.) (Step 1 in FIG. 5). Then the reactor 1 is brought into face-to-face contact with the second temperature-controlling block 7 having a fixed temperature-controlling surface 71 kept at a room temperature $t_1$ (Step 2 in FIG. 5). Further, the reactor 1 is brought into face-to-face contact with the third temperature-controlling block 8 having a fixed temperature-controlling surface 81 kept at a temperature $t_1$ (60° C.) (Step 3 in FIG. 5). A cycle of Steps 1 to 3 is repeated N times. After the completion of the N cycles, the reactor 1 is stopped at the detection position, and the optical detection is conducted.

With this reaction apparatus, the reactor 1 is delivered successively to the plural temperature-controlling blocks 6, 7, 8 according to a prescribed sequence program (e.g., for time control) as shown in FIG. 5A. Thereby, the temperature of the reaction liquid can readily be changed to a different temperature state rapidly and kept at that temperature for a prescribed time, and the temperature of the reaction liquid can be controlled stably with high accuracy, advantageously.

After completion of the reaction cycles, or during the reaction cycles if necessary, the progress of the reaction can be simply measured optically at the third stopping position shown in FIG. 5B.

The thermal cycling reaction apparatus and the reactor therefor has the advantages as set forth below:

(1) The temperature of the reaction liquid can be changed rapidly between plural prescribed temperatures, thereby the time of the repeated cycling reaction can be shortened.

(2) The temperature in the reaction chambers can be made uniform as a whole, and variation among the samples are made smaller.

(3) The temperature of the reaction liquid can be raised or lowered to a prescribed temperature without overshooting, whereby the follow-up control can be facilitated or omitted, and the reaction liquid can readily be controlled to be at a prescribed temperature for a prescribed time with higher accuracy to ensure stable control of the reaction.

(4) The small reactor holding a small amount of a reaction liquid enables miniaturization of the temperature controller, and miniaturization of the entire apparatus.

(5) In practice of PCR, the preheating can be substantially omitted to shorten the reaction time, and further preliminary incorporation of an intercalating fluorescent substance into the reaction liquid prior to PCR allows monitoring of the amplification degree with the reaction chamber completely sealed.

What is claimed is:

1. A reactor for a thermal cycling reaction, the reactor being able to be delivered along a delivery path having plural and separate temperature-controlling blocks fixed thereon, each of said temperature controlling blocks respectively having a fixed temperature-controlling surface of a prescribed area at a controlled temperature, the reactor being capable of repeatedly contacting successively in a predetermined order with a selected temperature controlling block, said reactor comprising a reactor body being in a shape of a plate, said reactor body having a heat-transferring area on at least one face of the plate to be brought into face-to-face contact with the respective temperature-controlling surfaces, said reactor body further having a cavity which forms a reaction chamber, said cavity having an opening on at least one face of the plate, wherein a heat-resistant sealing sheet for sealing the reaction chamber covers the opening of the chamber;

wherein the reactor further comprises a delivery-assisting member which carries the reactor body, said delivery-assisting member being composed of a poor heat-conductive material, the reactor body and the delivery-assisting member being formed in a plate shape.

2. The reactor of claim 1, wherein the sealing sheet is a heat-resistant transparent sheet which forms a transparent window for optically detecting a change in the reaction chamber from the outside.

3. The reactor of any one of claims 1 to 2, wherein said reaction chamber has a sealable liquid-filling opening for filling the reaction chamber with a reaction liquid.

4. The reactor of any of claims 1 to 2, wherein the reactor body is in a shape of a plate which has a thickness ranging from 0.2 to 3 mm.

5. A thermal cycling reaction apparatus, comprising a reactor of any one of claims 1 to 2; the thermal cycling reaction apparatus comprising said delivery path which guides the reactor; said plural temperature-controlling blocks placed apart from each other so as not to cause a thermal interaction along the delivery path and having respectively said fixed temperature-controlling surface of a prescribed area to be brought into contact with the reactor; a temperature controlling means for maintaining the temperature-controlling surfaces of the temperature-controlling blocks at respectively prescribed temperatures; and a driving means for delivering the reactor to each of the temperature controlling blocks so as to repeatedly contact each of the fixed temperature-controlling surfaces of the temperature-controlling blocks in a predetermined order.

6. The thermal cycling reaction apparatus of claim 5, wherein said delivery path includes a stopping position for the reactor that is different from positions of the temperature-controlling blocks on the delivery path; and further comprising an optical detecting means for detecting optically a change in the sealed reactor from the outside through the sealing sheet.

7. The thermal cycling reaction apparatus of claim 5, wherein the plural temperature-controlling blocks are placed separately along the delivery path.

8. The thermal cycling reaction apparatus of claim 5, for use for PCR, wherein a first temperature-controlling block of said temperature controlling blocks has a fixed first temperature-controlling surface kept at a dissociation temperature for a DNA having a target DNA sequence to dissociate a double-stranded DNA into a single-stranded DNA, a second temperature-controlling block of said temperature controlling blocks has a fixed second temperature-controlling surface kept at an annealing temperature for the single-stranded DNA to anneal thereto a forward primer and a reverse primer, and a third temperature-controlling block of said temperature controlling blocks has a fixed third temperature-controlling surface kept at a temperature for synthesizing another DNA strand complementary to the single-stranded DNA; and the delivery means is constructed so as to deliver the reactor to the first, second and third fixed temperature-controlling surfaces, and repeats this cycle a number of times.

9. The reactor according to claim 1, wherein said delivery-assisting member comprises a hole, said reactor body being fitted in said hole of said delivery-assisting member.

10. A reactor for a thermal cycling reaction, the reactor being able to be delivered along a delivery path having plural and separate temperature-controlling blocks fixed thereon, each of said temperature controlling blocks respectively having a fixed temperature-controlling surface of a prescribed area at a controlled temperature, the reactor repeatedly contacting successively in a predetermined order with a selected temperature controlling block, said reactor comprising a reactor body being in a shape of a plate, said reactor body having a heat-transferring area on at least one face of the plate to be brought into face-to-face contact with the respective temperature-controlling surfaces, said reactor body further having a cavity which forms a reaction chamber, said cavity having an opening on at least one face of the plate, wherein a heat-resistant sealing sheet for sealing the reaction chamber covers the opening of the chamber, and the reactor body has a thickness ranging from 0.2 to 3 mm.

11. A thermal cycling reaction apparatus comprising:

a reactor for a thermal cycling reaction, said reactor comprising a reactor body with a heat-transferring area, said reactor body comprising a cavity which forms a reaction chamber, wherein a heat-resistant sealing sheet covers the reaction chamber so as to seal the reaction chamber;

a delivery path for guiding the reactor past a plurality of temperature controlling blocks which make contact with the reactor, wherein the plurality of temperature controlling blocks are positioned along said delivery path, each of said temperature controlling blocks having a temperature controlling surface of a prescribed area;

a temperature controlling means for maintaining the temperature controlling surfaces of the temperature controlling blocks at prescribed temperatures; and driving means for conveying the reactor along said delivery path so as to bring the heat-transferring area of the reactor body into contact in a predetermined order with each of the temperature-controlling surfaces of each of the temperature controlling blocks.

* * * * *